United States Patent
Abdou

(10) Patent No.: US 8,673,013 B2
(45) Date of Patent: Mar. 18, 2014

(54) DEVICES AND METHODS FOR INTER-VERTEBRAL ORTHOPEDIC DEVICE PLACEMENT

(71) Applicant: Samy Abdou, San Diego, CA (US)

(72) Inventor: Samy Abdou, San Diego, CA (US)

(73) Assignee: Samy Abdou, San Diego, CA (US)

( * ) Notice: Subject to any disclaimer, the term of this patent is extended or adjusted under 35 U.S.C. 154(b) by 0 days.

(21) Appl. No.: 13/657,597

(22) Filed: Oct. 22, 2012

(65) Prior Publication Data

US 2013/0110246 A1    May 2, 2013

Related U.S. Application Data

(63) Continuation of application No. 12/690,824, filed on Jan. 20, 2010, now Pat. No. 8,292,896, which is a continuation of application No. 11/245,466, filed on Oct. 5, 2005, now Pat. No. 7,951,153.

(60) Provisional application No. 60/616,100, filed on Oct. 5, 2004.

(51) Int. Cl.
*A61F 2/44* (2006.01)

(52) U.S. Cl.
USPC .................... 623/17.16; 623/17.11; 606/99

(58) Field of Classification Search
USPC .................... 623/17.11, 17.16; 606/99
See application file for complete search history.

(56) References Cited

U.S. PATENT DOCUMENTS

| | | | |
|---|---|---|---|
| 3,090,386 A | 5/1963 | Babcock | |
| 4,037,592 A | 7/1977 | Kronner | |
| 4,289,123 A | 9/1981 | Dunn | |
| 4,569,662 A | 2/1986 | Dragan | |
| 4,580,563 A | 4/1986 | Gross | |
| 4,722,331 A | 2/1988 | Fox | |
| 4,899,761 A | 2/1990 | Brown et al. | |
| 4,907,577 A | 3/1990 | Wu | |
| 5,133,717 A | 7/1992 | Chopin | |
| 5,254,118 A | 10/1993 | Mirkovic | |
| 5,330,468 A | 7/1994 | Burkhart | |
| 5,334,205 A | 8/1994 | Cain | |
| 5,545,164 A | 8/1996 | Howland | |
| 5,569,248 A | 10/1996 | Mathews | |
| 5,609,634 A | 3/1997 | Voydeville | |
| 5,616,142 A | 4/1997 | Yuan et al. | |

(Continued)

FOREIGN PATENT DOCUMENTS

| | | |
|---|---|---|
| DE | 10035182 | 2/2002 |
| EP | 77159 | 4/1983 |

(Continued)

OTHER PUBLICATIONS

Derwent English Language Abstract WPI Acct. No. 2002-155861-200221 for German Patent No. DE10035182 (Item CV).
Denis, F. "The three column spine and its significance in the classification of acute thoracolumbar spinal injuries" Spine Nov.-Dec. 1983; 8(8):817-831.

*Primary Examiner* — Christian Sevilla
(74) *Attorney, Agent, or Firm* — Gazdzinski & Associates, PC

(57) ABSTRACT

Disclosed are methods and devices for implanting an orthopedic device between skeletal segments, such as vertebrae, using limited surgical dissection. The implanted devices are used to adjust and maintain the spatial relationships of adjacent bones. The implanted device can be, for example, an artificial disc, a fusion cage or any other appropriate device for implantation between skeletal segments.

24 Claims, 14 Drawing Sheets

(56) References Cited

U.S. PATENT DOCUMENTS

| | | | |
|---|---|---|---|
| 5,645,599 A | 7/1997 | Samani | |
| 5,672,176 A | 9/1997 | Biedermann et al. | |
| 5,681,312 A | 10/1997 | Yuan et al. | |
| 5,928,139 A | 7/1999 | Koros et al. | |
| 5,928,233 A | 7/1999 | Apfelbaum et al. | |
| 5,993,449 A | 11/1999 | Schlapfer et al. | |
| 6,039,761 A | 3/2000 | Li et al. | |
| 6,090,113 A | 7/2000 | Le Couedic et al. | |
| 6,123,707 A | 9/2000 | Wagner | |
| 6,159,244 A | 12/2000 | Suddaby | |
| 6,193,757 B1 | 2/2001 | Foley et al. | |
| 6,306,136 B1 | 10/2001 | Baccelli | |
| 6,312,431 B1 | 11/2001 | Asfora | |
| 6,319,002 B1 | 11/2001 | Pond | |
| 6,319,257 B1 | 11/2001 | Carignan | |
| 6,355,038 B1 | 3/2002 | Pisharodi | |
| 6,387,130 B1 * | 5/2002 | Stone et al. | 623/17.16 |
| 6,419,676 B1 | 7/2002 | Zucherman et al. | |
| 6,419,677 B2 | 7/2002 | Zucherman et al. | |
| 6,428,576 B1 | 8/2002 | Haldimann | |
| 6,440,133 B1 | 8/2002 | Beale | |
| 6,451,019 B1 | 9/2002 | Zucherman et al. | |
| 6,451,020 B1 | 9/2002 | Zucherman et al. | |
| 6,508,839 B1 | 1/2003 | Lambrecht et al. | |
| 6,524,315 B1 | 2/2003 | Selvitelli et al. | |
| 6,530,929 B1 | 3/2003 | Justis et al. | |
| 6,547,790 B2 | 4/2003 | Harckey, III et al. | |
| 6,558,386 B1 | 5/2003 | Cragg | |
| 6,558,390 B2 | 5/2003 | Cragg | |
| 6,599,294 B2 | 7/2003 | Fuss | |
| 6,599,295 B1 | 7/2003 | Tornier et al. | |
| 6,695,842 B2 | 2/2004 | Zucherman et al. | |
| 6,716,212 B1 | 4/2004 | Pickens | |
| 6,730,126 B2 | 5/2004 | Boehm, Jr. et al. | |
| 6,733,534 B2 | 5/2004 | Sherman | |
| 6,739,068 B1 | 5/2004 | Rinner | |
| 6,740,087 B2 | 5/2004 | Knox | |
| 6,740,090 B1 | 5/2004 | Cragg et al. | |
| 6,746,449 B2 | 6/2004 | Jones | |
| 6,749,614 B2 | 6/2004 | Teitelbaum et al. | |
| 6,755,841 B2 | 6/2004 | Fraser | |
| 6,761,720 B1 | 7/2004 | Senegas | |
| 6,783,547 B2 | 8/2004 | Castro | |
| 6,790,210 B1 | 9/2004 | Cragg et al. | |
| 6,805,697 B1 | 10/2004 | Helm et al. | |
| 6,821,277 B2 | 11/2004 | Teitelbaum | |
| 6,875,211 B2 | 4/2005 | Nichols et al. | |
| 6,899,716 B2 | 5/2005 | Cragg | |
| 6,921,403 B2 | 7/2005 | Cragg et al. | |
| 6,945,975 B2 | 9/2005 | Dalton et al. | |
| 7,008,422 B2 | 3/2006 | Foley et al. | |
| 7,011,660 B2 | 3/2006 | Sherman et al. | |
| 7,014,633 B2 | 3/2006 | Cragg | |
| 7,060,066 B2 | 6/2006 | Zhao et al. | |
| 7,087,058 B2 | 8/2006 | Cragg | |
| 7,118,579 B2 | 10/2006 | Michelson | |
| 7,153,281 B2 | 12/2006 | Holmes | |
| 7,160,300 B2 | 1/2007 | Jackson | |
| 7,232,463 B2 | 6/2007 | Falahee | |
| 7,455,685 B2 | 11/2008 | Justis | |
| 7,572,276 B2 | 8/2009 | Lim et al. | |
| 7,585,316 B2 | 9/2009 | Trieu | |
| 2001/0012938 A1 | 8/2001 | Zucherman | |
| 2001/0053914 A1 | 12/2001 | Landry et al. | |
| 2002/0045904 A1 * | 4/2002 | Fuss et al. | 606/99 |
| 2002/0049444 A1 | 4/2002 | Knox | |
| 2002/0055741 A1 | 5/2002 | Schlapfer et al. | |
| 2002/0077530 A1 | 6/2002 | Velikaris et al. | |
| 2002/0099386 A1 | 7/2002 | Beger et al. | |
| 2002/0161368 A1 | 10/2002 | Foley | |
| 2002/0183755 A1 | 12/2002 | Michelson et al. | |
| 2003/0018389 A1 | 1/2003 | Castro et al. | |
| 2003/0074005 A1 | 4/2003 | Roth et al. | |
| 2003/0078583 A1 | 4/2003 | Biedermann et al. | |
| 2003/0187436 A1 | 10/2003 | Bolger et al. | |
| 2003/0229347 A1 | 12/2003 | Sherman et al. | |
| 2003/0236472 A1 | 12/2003 | Van Hoeck et al. | |
| 2004/0044412 A1 | 3/2004 | Lambrecht | |
| 2004/0133207 A1 | 7/2004 | Abdou | |
| 2004/0138671 A1 | 7/2004 | Zander et al. | |
| 2004/0167625 A1 | 8/2004 | Beyar et al. | |
| 2004/0204713 A1 | 10/2004 | Abdou | |
| 2005/0004573 A1 | 1/2005 | Abdou | |
| 2005/0021029 A1 | 1/2005 | Trieu et al. | |
| 2005/0021031 A1 | 1/2005 | Foley et al. | |
| 2005/0021040 A1 | 1/2005 | Bertagnoli | |
| 2005/0085813 A1 | 4/2005 | Spitler et al. | |
| 2005/0119747 A1 | 6/2005 | Fabris Monterumici et al. | |
| 2005/0131421 A1 | 6/2005 | Anderson et al. | |
| 2005/0154389 A1 | 7/2005 | Selover et al. | |
| 2005/0171540 A1 | 8/2005 | Lim et al. | |
| 2005/0177163 A1 | 8/2005 | Abdou | |
| 2005/0192589 A1 | 9/2005 | Raymond | |
| 2005/0197660 A1 | 9/2005 | Haid et al. | |
| 2005/0203512 A1 | 9/2005 | Hawkins et al. | |
| 2005/0203533 A1 | 9/2005 | Ferguson et al. | |
| 2005/0203624 A1 | 9/2005 | Serhan | |
| 2005/0209694 A1 | 9/2005 | Loeb | |
| 2005/0215999 A1 | 9/2005 | Birkmeyer et al. | |
| 2005/0234449 A1 | 10/2005 | Aferzon | |
| 2005/0234451 A1 | 10/2005 | Markworth | |
| 2005/0245928 A1 | 11/2005 | Colleran | |
| 2005/0261768 A1 | 11/2005 | Trieu | |
| 2005/0273120 A1 | 12/2005 | Abdou | |
| 2005/0288669 A1 | 12/2005 | Abdou | |
| 2006/0036240 A1 | 2/2006 | Colleran et al. | |
| 2006/0052870 A1 | 3/2006 | Ferree | |
| 2006/0074488 A1 | 4/2006 | Abdou | |
| 2006/0084986 A1 | 4/2006 | Grinberg et al. | |
| 2006/0084988 A1 | 4/2006 | Kim | |
| 2006/0142761 A1 | 6/2006 | Landry et al. | |
| 2006/0149238 A1 | 7/2006 | Sherman et al. | |
| 2006/0149278 A1 | 7/2006 | Abdou | |
| 2006/0167454 A1 | 7/2006 | Ludwig et al. | |
| 2006/0184247 A1 | 8/2006 | Edidin et al. | |
| 2006/0195102 A1 | 8/2006 | Malandain | |
| 2006/0217710 A1 | 9/2006 | Abdou | |
| 2006/0229614 A1 | 10/2006 | Foley et al. | |
| 2006/0229615 A1 | 10/2006 | Abdou | |
| 2006/0247630 A1 | 11/2006 | Iott et al. | |
| 2006/0264942 A1 | 11/2006 | Lim et al. | |
| 2006/0276803 A1 | 12/2006 | Salerni | |
| 2007/0032790 A1 | 2/2007 | Aschmann et al. | |
| 2007/0093828 A1 | 4/2007 | Abdou | |
| 2007/0106383 A1 | 5/2007 | Abdou | |
| 2007/0123884 A1 | 5/2007 | Abdou | |
| 2007/0151116 A1 | 7/2007 | Malandain | |
| 2008/0027438 A1 | 1/2008 | Abdou | |
| 2010/0016906 A1 | 1/2010 | Abdou | |
| 2010/0069929 A1 | 3/2010 | Abdou | |
| 2010/0106250 A1 | 4/2010 | Abdou | |

FOREIGN PATENT DOCUMENTS

| | | |
|---|---|---|
| EP | 0611116 | 8/1994 |
| EP | 1442715 | 8/2004 |
| WO | 2004/032726 | 4/2004 |
| WO | 2004/062482 | 7/2004 |
| WO | 2004/093702 | 11/2004 |
| WO | 2005/077288 | 8/2005 |
| WO | 2005/122922 | 12/2005 |
| WO | 2006/041963 | 4/2006 |
| WO | 2006/058221 | 6/2006 |
| WO | 2006/089292 | 8/2006 |
| WO | 2006/096756 | 9/2006 |
| WO | 2007/041648 | 4/2007 |
| WO | 2007/044705 | 4/2007 |
| WO | 2007/044836 | 4/2007 |
| WO | 2007/056516 | 5/2007 |
| WO | 2007/059207 | 5/2007 |

* cited by examiner

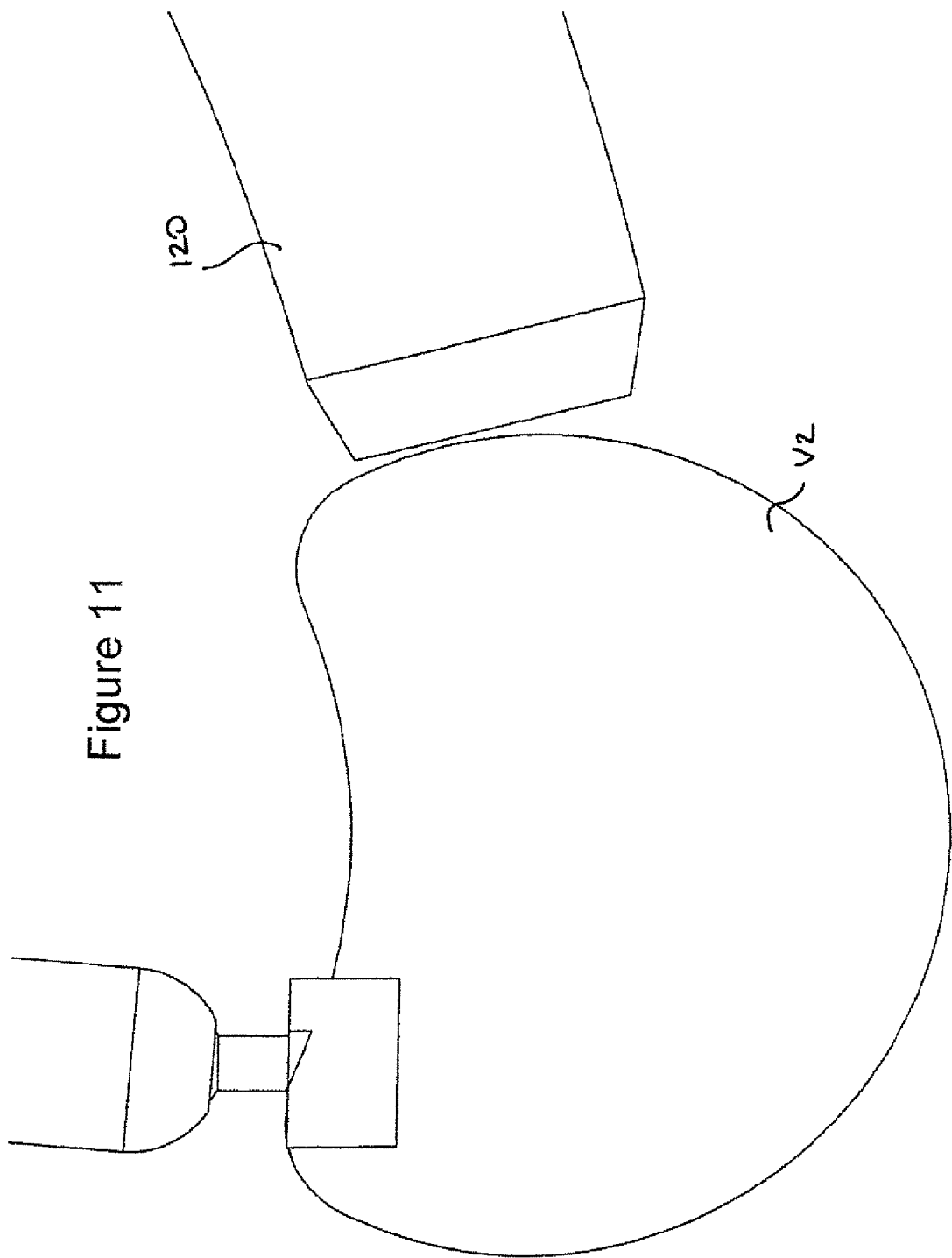

DEVICES AND METHODS FOR INTER-VERTEBRAL ORTHOPEDIC DEVICE PLACEMENT

REFERENCE TO PRIORITY DOCUMENT

This application is a continuation of and claims priority to U.S. patent application Ser. No. 12/690,824, filed on Jan. 20, 2010, and entitled "Devices and Methods for Intervertebral Orthopedic Device Placement," which issued as U.S. Pat. No. 8,292,896 on Oct. 23, 2012, which is a continuation of and claims priority to U.S. patent application Ser. No. 11/245,466, filed Oct. 5, 2005, entitled "Devices and Methods for Inter-vertebral Orthopedic Device Placement," which issued as U.S. Pat. No. 7,951,153 on May 31, 2011, and which claims priority of U.S. Provisional Patent Application Ser. No. 60/616,100, filed Oct. 5, 2004. Priority of the aforementioned filing dates is hereby claimed, and the disclosures of the Applications are hereby incorporated by reference in their entirety.

BACKGROUND

The disclosure relates to devices and methods for implantation of an orthopedic device between skeletal segments using limited surgical dissection. The implanted devices are used to adjust and maintain the spatial relationship(s) of adjacent bones. Depending on the design of the implant, the skeletal segments may be immobilized or motion between them may be preserved.

Surgical reconstructions of the bony skeleton are common procedures in current medical practice. Regardless of the anatomical region or the specifics of the reconstructive procedure, many surgeons employ an implantable device between bony segments in order to adjust, align and maintain the spatial relationship(s) between them.

Placement of an inter-vertebral device within the spine may be performed through various approaches. Access to the anterior aspect of the spine provides a direct route for device placement. However, since the spine is situated posteriorly within the body cavity, an anterior approach requires dissection through the many vital tissues that lie anterior to the spine. Likewise, a lateral approach also requires extensive dissection of the body cavity. Both approaches are more difficult in the thoracic and lumbar spine, since these body cavities contain far more tissue anterior and lateral to the spine.

A posterior approach provides ready access to the posterior aspect of the spine through an operative corridor that is familiar to all spine surgeons. Unfortunately, the nerve elements are situated posterior to the intervertebral space and will limit access to that space. Hence, use of the posterior approach for the placement of any sizable device within the inter-vertebral space risks permanent neurologic injury.

SUMMARY

In view of the proceeding, there is a need for devices and methods for delivery of inter-vertebral implants that do not require extensive dissection of normal tissues or significant retraction of the nerve elements. Such devices and methods provide ease of use as well as a safe and familiar surgical approach that maximizes the likelihood of optimal device placement within the inter-vertebral space.

The spine is posteriorly situated within the body cavity and can be readily reached with minimal tissue dissection using a posterior skin incision. This approach is direct, safe, simple and familiar to all spine surgeons. Unfortunately, the neural elements that reside within the spinal canal will permit only limited access to the anteriorly-placed inter-vertebral disc space. Access is gained through a small window lateral to the nerves. While this window can be used to safely remove disc material and place small inter-vertebral devices, attempts at placement of any sizable device risks permanent nerve injury.

Disclosed is a device that can accurately place a sizable implant within the inter-vertebral space without the extensive tissue dissection currently required to access this region.

The spine is approached through a posterior incision permitting access to the inter-vertebral disc space through the window lateral to the nerves. A discectomy is performed and the disc material is removed piecemeal. An instrument is placed into the disc space through the lateral window. The distal end of the instrument is attached to a curvilinear guide. The guide arm is then rotated about the distal end of the instrument until the tip of the guide arm abuts the side of the disc space. In this way, the guide arm can be used to guide an orthopedic device into the disc space with minimal tissue dissection. In other embodiments, instruments are attached to the spinous processes, pedicles or other bony land marks. The guide arm is connected to the distal end of the instrument(s) and the guide arm is rotated into position.

In one aspect, there is disclosed an instrument for implanting an implant device in a space between a pair of skeletal segments. The instrument can comprise a mount having a distal end mountable between the pair of skeletal segments, and an insertion device pivotably attached to a proximal end of the mount. The insertion device is pivotable to an orientation so as to deliver an implant into the space between the pair of skeletal segments.

In another aspect, there is disclosed an instrument for implanting an implant device into a space between skeletal segments. The instrument can comprise an insertion device having a delivery shaft, wherein the insertion device can be pivotably mounted in a predetermined spatial relationship relative to the space between the skeletal segments. The insertion device pivots to a delivery orientation such that the delivery shaft provides a pathway for the delivery of an orthopedic device into the space between the skeletal segments.

In another aspect, there is disclosed a device for use in a surgical procedure, comprising at least one anchor that anchor relative to a target location; and an insertion device connected to the at least one anchor, the insertion device movable in a fixed geometric relation to the at least one anchor so as to place an implant at the target location.

In another aspect, there is disclosed a device for use in a surgical procedure, comprising at least one anchor that anchor relative to a target location and an insertion device movably attached to the anchor. The insertion device is movable in a fixed geometric relationship relative to the at least one anchor so as to place the implant in the target location. The position of target location is defined using x-ray guidance.

The placement system described herein provides an easy and reliable way of placing sizable orthopedic device(s) within the inter-vertebral with minimal tissue dissection. The implanted devices may include, for example, artificial discs, fusion cages or any other appropriate device.

In another aspect, a method for delivery of an orthopedic implant onto a target intervertebral disc space of a subject is disclosed. In one embodiment, the method includes: (i) approaching the target intervertebral disc space through a posterior skin incision and a surgical corridor, (ii) performing at least a partial discectomy is through a posterior window immediately lateral to nerve elements adjacent to the target intervertebral disc space, (iii) positioning a segment of an implant insertion member in proximity to a site of the discectomy, the implant insertion member comprising an elongated body extending along a curvilinear trajectory, the elongated body comprising an internal bore configured to permit advancement of the orthopedic implant therethrough, (iv) attaching a first end of a fixation member to a proximal segment of the implant insertion member, the fixation member comprising a locking feature configured to reversibly immobilize the first end of the fixation member and at least a portion of the implant insertion member, (v) attaching a second end of the fixation member rigidly onto a coupling apparatus having a defined spatial relationship to the target intervertebral disc space, attachment thereof limiting movement of the implant insertion member relative to the target intervertebral disc space in at least one plane (vi) rotating the implant insertion member relative to the fixation member from a location outside the subject to a lateral side aspect of the target intervertebral disc space, and (vii) advancing the orthopedic implant through the internal bore of the implant insertion member and onto the target intervertebral disc space.

In a second embodiment, the method includes: (i) performing at least a partial discectomy through a window immediately lateral to nerve elements adjacent to the target disc space, (ii) positioning a segment of an implant insertion member in proximity to the target disc space, (iii) attaching a first end of a fixation member to a proximal segment of the implant insertion member, the attachment permitting reversible immobilization of the first end of the fixation member and the proximal segment of the implant insertion member, (iv) rigidly attaching a second end of the fixation member onto a first surface having a defined spatial relationship to the target disc space, the attachment limiting movement of the implant insertion member relative to the target disc space in at least one plane, and (v) advancing the orthopedic implant through an internal bore of the implant insertion member and onto a lateral side aspect of the target disc space. The implant insertion member comprises an elongated body extending along a first direction from a proximal segment to a distal segment. The elongated body comprises the internal bore, and the internal bore is configured to extend at least partially along the first direction in a curvilinear trajectory.

In yet another embodiment, the method includes performing at least a partial discectomy through a posterior window lateral to nerve elements adjacent to the target intervertebral disc space; positioning a segment of an implant insertion member in proximity to a site of the discectomy, the implant insertion member comprising an elongated body extending along an at least partly curvilinear trajectory, the elongated body comprising an internal bore configured to permit advancement of the orthopedic implant therethrough; attaching a first end of a fixation member to a segment of the implant insertion member, the fixation member comprising a locking feature configured to reversibly immobilize the first end of the fixation member and at least a portion of the implant insertion member; attaching a second end of the fixation member rigidly onto a coupling apparatus having a spatial relationship to the target intervertebral disc space, attachment thereof limiting movement of the implant insertion member relative to the target intervertebral disc space in at least one plane; rotating the implant insertion member relative to the fixation member to a lateral side aspect of the target intervertebral disc space; and advancing the orthopedic implant through the internal bore of the implant insertion member and into the target intervertebral disc space.

These and other features will become more apparent from the following description and certain modifications thereof when taken with the accompanying drawings.

BRIEF DESCRIPTION OF THE DRAWINGS

FIG. 11 shows an enlarged, close-up view with a distal tip of the insertion device positioned adjacent the lateral side of the disc space between the vertebrae.

DETAILED DESCRIPTION

Disclosed are methods and devices for implanting an implant device (such as an orthopedic device) between skeletal segments (such as vertebrae), using limited surgical dissection. The implanted devices are used to adjust and maintain the spatial relationship(s) of adjacent bones. The implanted device can be, for example, an artificial disc, a fusion cage or any other appropriate device for implantation between skeletal segments.

Figure 1:
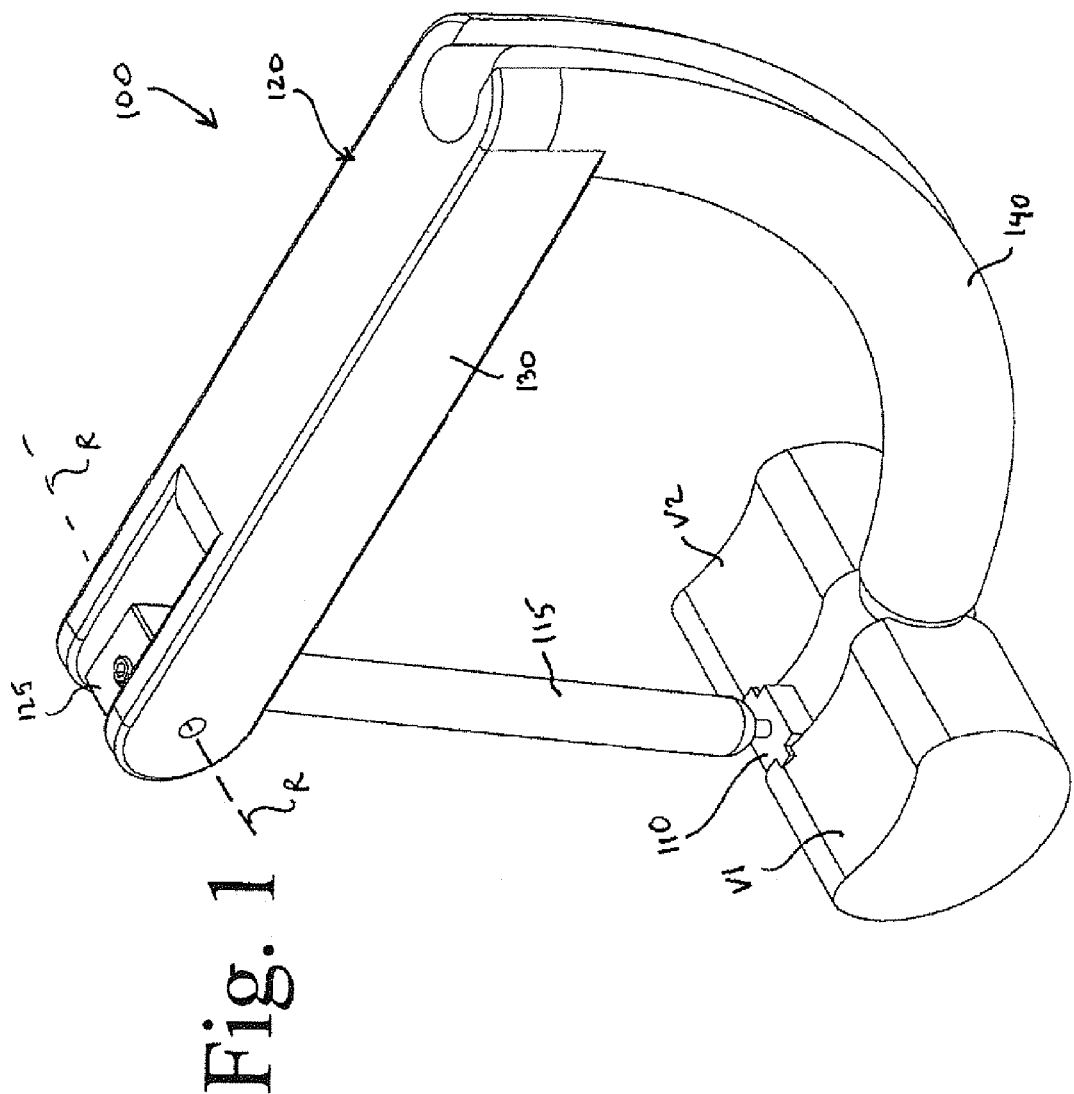
FIG. 1 shows a perspective, assembled view of a device for implanting an orthopedic device between skeletal segments, such as between a first vertebra V1 and a second vertebra V2.
Figure 2:
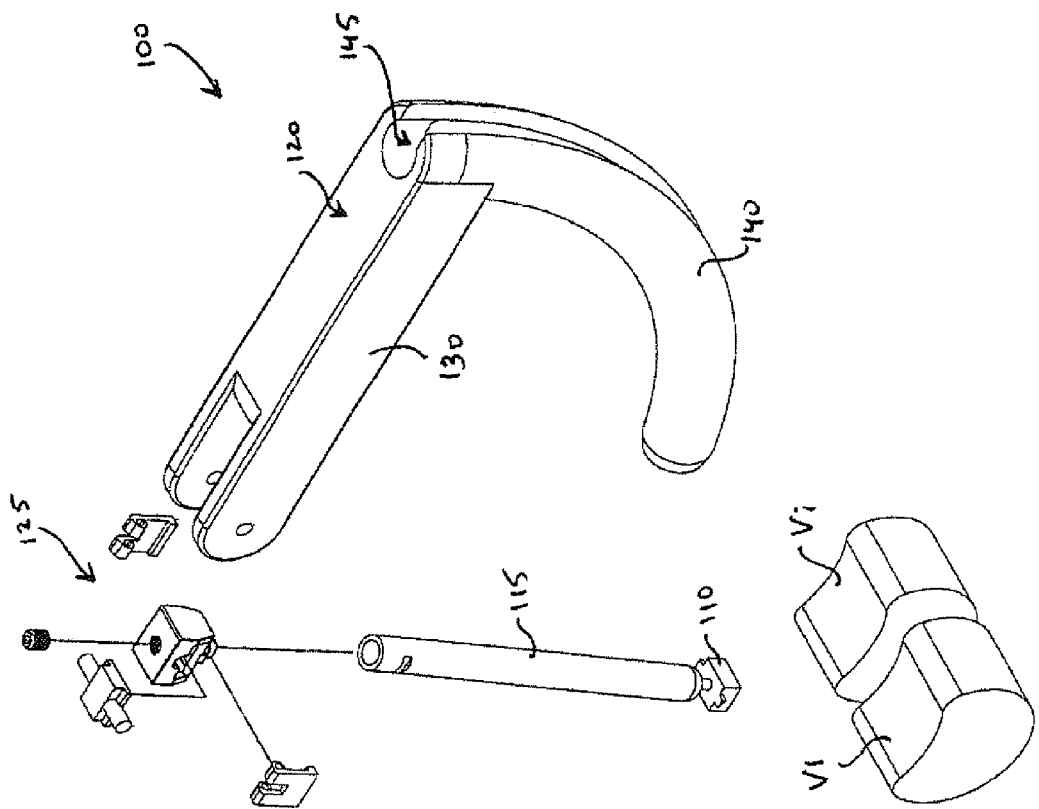
FIG. 2 shows the device 100 in an exploded state and uncoupled from the first vertebra V1 and second vertebra V2.

FIG. 1 shows a perspective, assembled view of a device 100 for implanting an orthopedic device between skeletal segments, such as between a first vertebra Vi and a second vertebra V2. In FIG. 1, a coupler of the device 100 is positioned in a disc space between the first vertebra Vi and second vertebra V2. FIG. 2 shows the device 100 in an exploded state and uncoupled from the first vertebra Vi and second vertebra V2. For clarity of illustration, the vertebrae are represented schematically and those skilled in the art will appreciate that actual vertebrae include anatomical details not shown in FIG. 1. Moreover, although described in the context of being used with vertebrae, it should be appreciated the device 100 and associated methods can also be used with other skeletal segments.

The device 100 includes a coupler 110, a elongate mount 115, and an insertion device 120 that is pivotably attached to a proximal end of the mount 115 via an attachment member 125. The mount 115 is used to attach the insertion device 120 to the coupler 110.

The coupler 110 is a device that anchors to a predetermined location relative to a skeletal segment. For example, the coupler 110 can anchor to the one or more of the vertebrae or to the disc space between a pair of vertebrae. In one embodiment, the coupler 110 is sized and shaped to be positioned within and removably secured within the disc space between the two vertebrae. The coupler 110 can have any shape that is configured to be attached between two vertebrae. In the illustrated embodiment, the coupler 110 is rectangular shaped with a pair of outwardly-extending posts that abut at least a portion of the vertebrae.

With reference still to FIGS. 1 and 2, a mount 115 extends outwardly from the coupler 110. The mount 115 is an elongate member, such as a post, having a distal end attached to the coupler 110 and a proximal end pivotably attached to the insertion device 120. The mount 115 includes an inner member and an outer member, as described in detail below with reference to FIGS. 3 and 4.

The insertion member 120 is pivotably attached to the proximal end of the mount 115. The insertion member 120 includes a straight or substantially straight portion 130 that extends outwardly from the proximal end of the mount, and a curved portion 140 that curves toward the coupler 110 from an outward tip of the straight portion 130. The curved portion 140 includes a guide shaft 145 that extends through the curved portion 140 along the entire length of the curved portion 140. The radius of curvature of the curved portion 140 can vary. In one embodiment, the radius of curvature is approximately equal to the length of the straight portion 130. As described in detail below, the curved portion 140 acts as a guide for guiding an orthopedic device to a position between the skeletal segments.

As mentioned, an attachment member 125 pivotably attaches the insertion member 120 to the proximal end of the mount 115. The attachment member 125 is configured to permit the insertion member 120 to pivot about a pivot axis R (shown in FIG. 1). An exemplary embodiment of the attachment member 125 is described in detail below, although it should be appreciated that the structural configuration of the attachment member 125 can vary.

Figure 3:
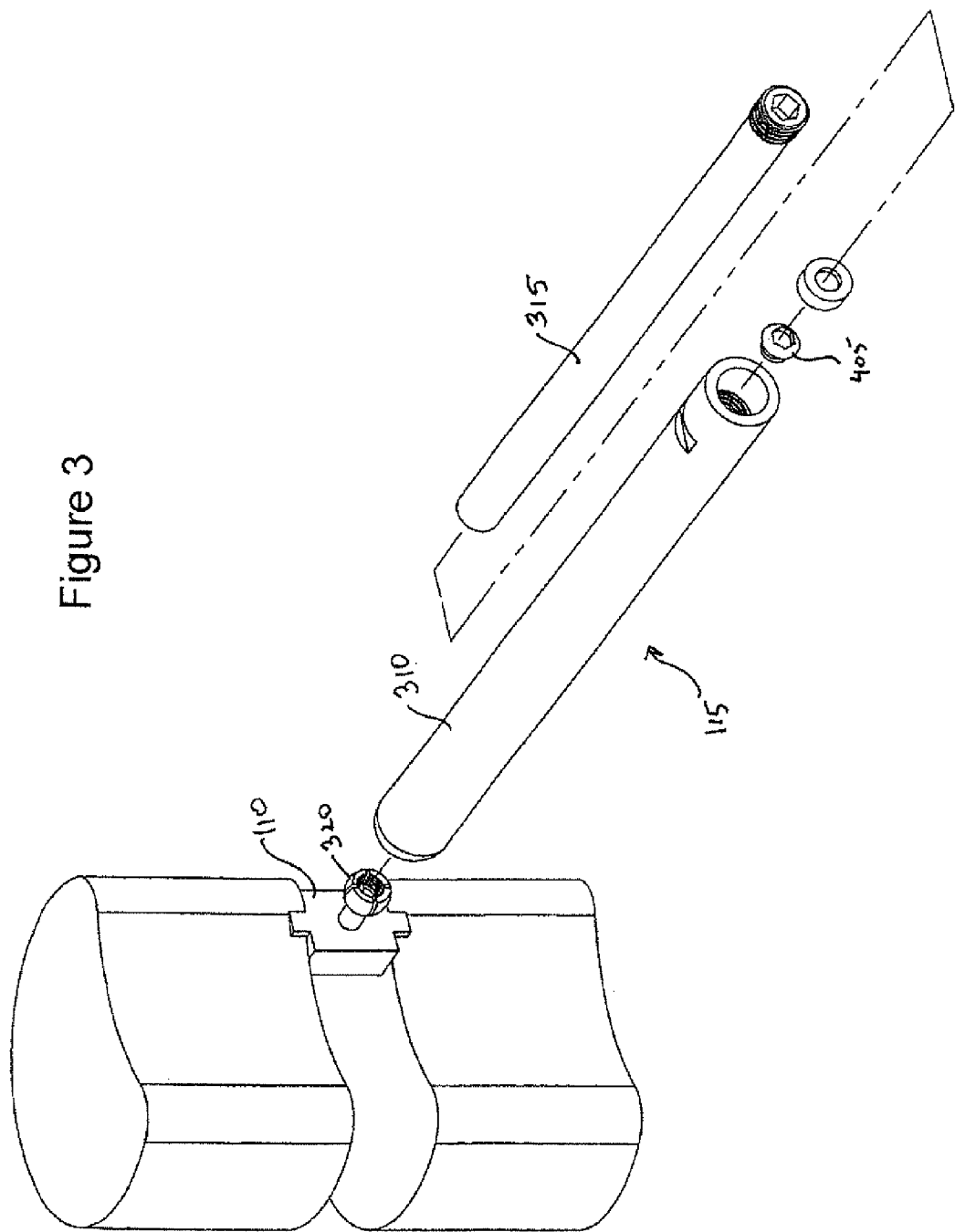
FIG. 3 shows an exploded view of a mount that attaches the insertion member of the device to a coupler of the device.

FIG. 3 shows an exploded view of the mount 115 that attaches the insertion member 120 to the coupler 110. For clarity of illustration, the insertion member 120 is not shown in FIG. 3. As mentioned, the mount 115 includes an outer member 310 and an inner member 315 that can be slidably and axially positioned inside the outer member 310. The outer member 310 is sized to fit over a head 320 of the coupler 110 in a press fit fashion to thereby permit the mount 115 to be removably coupled to the coupler 110.

Figure 4:
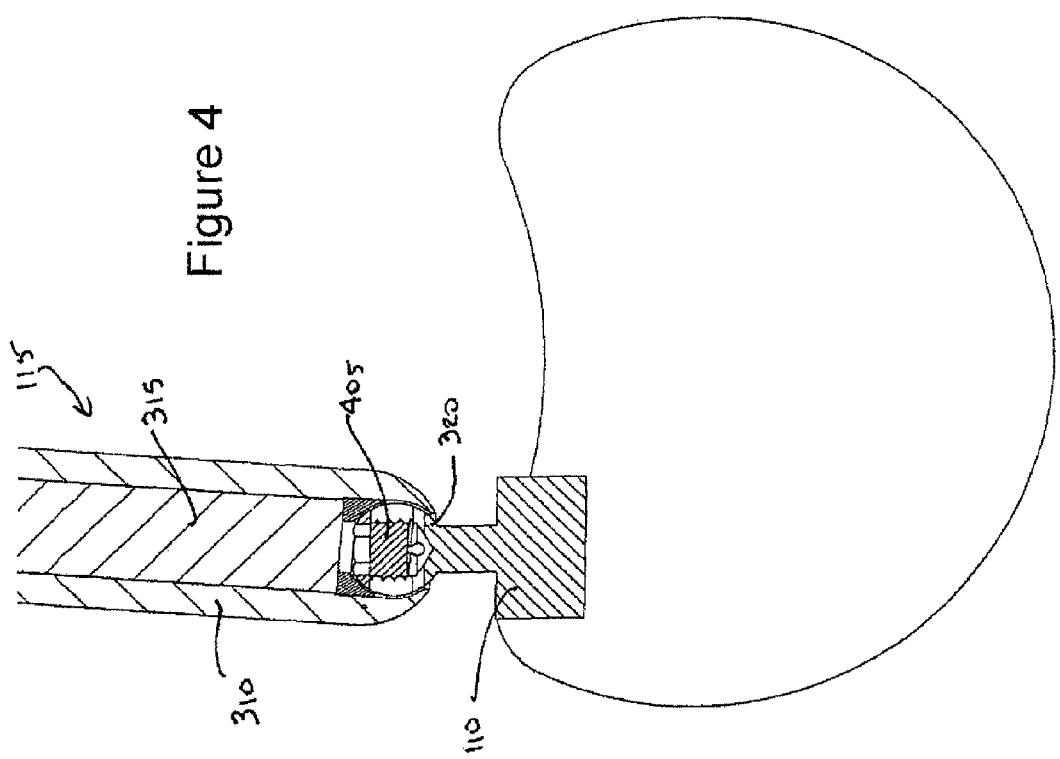
FIG. 4 shows a cross-sectional view of the mount coupled to the coupler.

FIG. 4 shows a cross-sectional view of the mount 115 coupled to the coupler 110. The outer member 310 is positioned over the head 320 such that the mount 115 extends outwardly from the coupler 110. Moreover, the outer member 310 is positioned over the head 320 such that the mount 115 can be pivoted relative to the coupler 110. A set screw 405 can be set into the head 320 of the coupler 110 to secure the mount 115 to the coupler 110. The inner member 315 is then inserted into the outer member 315 over the set screw 405. In this manner, the mount 115 is pivotably attached to the coupler 110.

Figure 5:
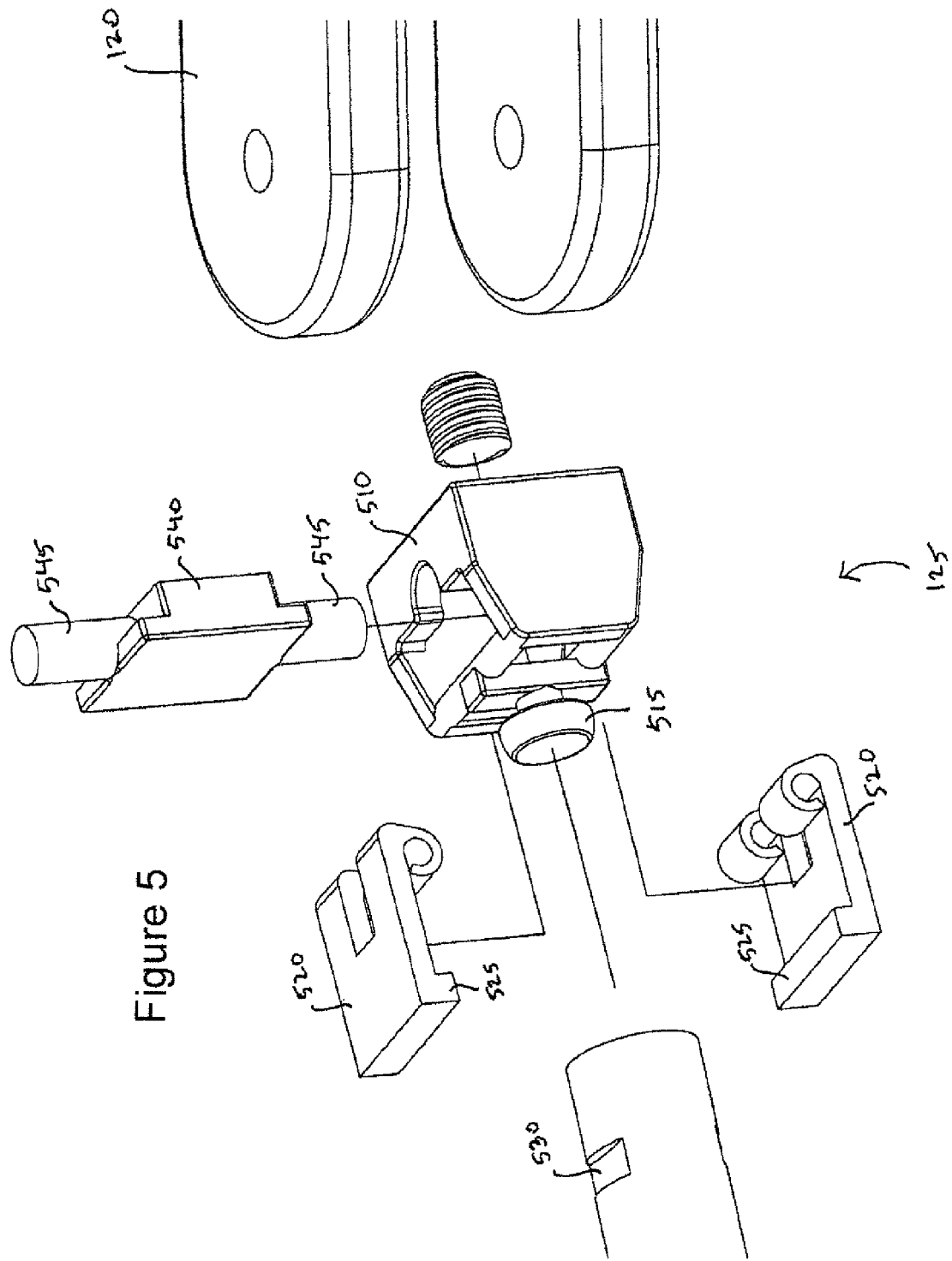
FIG. 5 shows an enlarged, exploded view of an attachment member positioned adjacent an attachment region of the insertion device.
Figure 6:
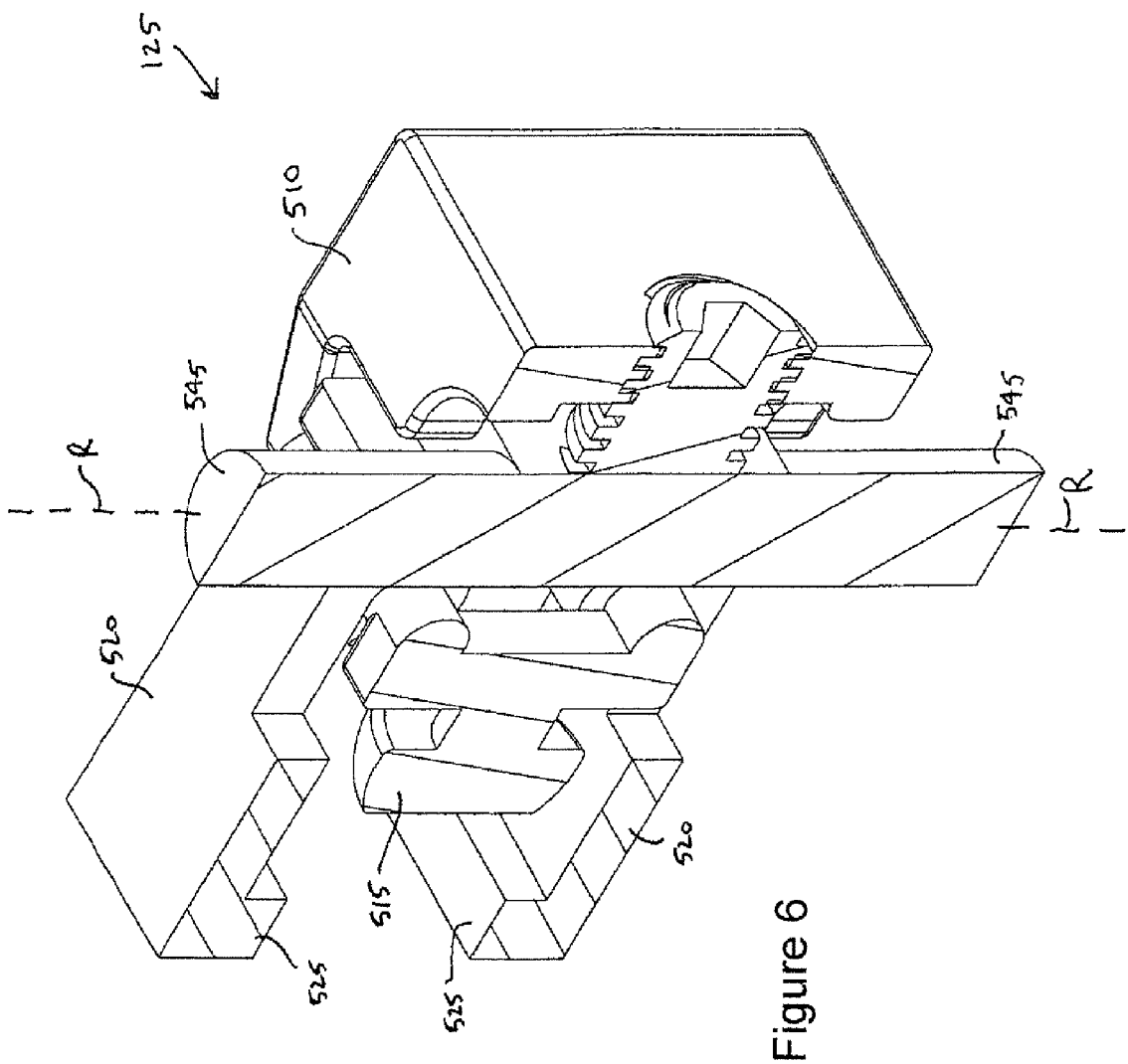
FIG. 6 shows a perspective, cross-sectional, assembled view of the attachment member.

As mentioned, the attachment member 125 is used to pivotably attach the insertion device 120 to the proximal end of the mount 115. FIG. 5 shows an enlarged, exploded view of the attachment member 125 positioned adjacent an attachment region of the insertion device 120. FIG. 6 shows a perspective, cross-sectional, assembled view of the attachment member 125, The attachment member 125 includes a main body 510 having a rounded protrusion 515 that can be positioned inside the proximal end of the mount 115, A pair of side walls 520 having inwardly extending teeth 525 are positioned on opposite sides of the main body 510, As mentioned, the structural configuration of the attachment member 125 can vary and is not limited to the embodiment described herein.

With reference to FIG. 5, the attachment member 125 is attached to the mount 115 by inserting the rounded protrusion 515 into the proximal end of the mount 115, The two side walls 520 are positioned on either side of the mount 115 such that each tooth 525 engages a corresponding slot 530 on the mount 515, In this manner, the attachment member 125 is attached to the mount 115.

With reference to FIGS. 5 and 6, a pivot rod member 540 is positionable inside the main body 510, The pivot rod member 540 includes a pivot rod 545 that protrude outwardly from opposed sides of the main body 510 when the pivot rod member 540 is positioned inside the main body 510, The pivot rod 545 can be inserted into a pair of apertures 555 on the insertion device 120 to pivotably couple the insertion device 120 to mount 115 via the attachment member 125. The pivot rod 545 defines the pivot axis R (FIGS. 1 and 6) for pivoting of the insertion device 120.

Figure 7:
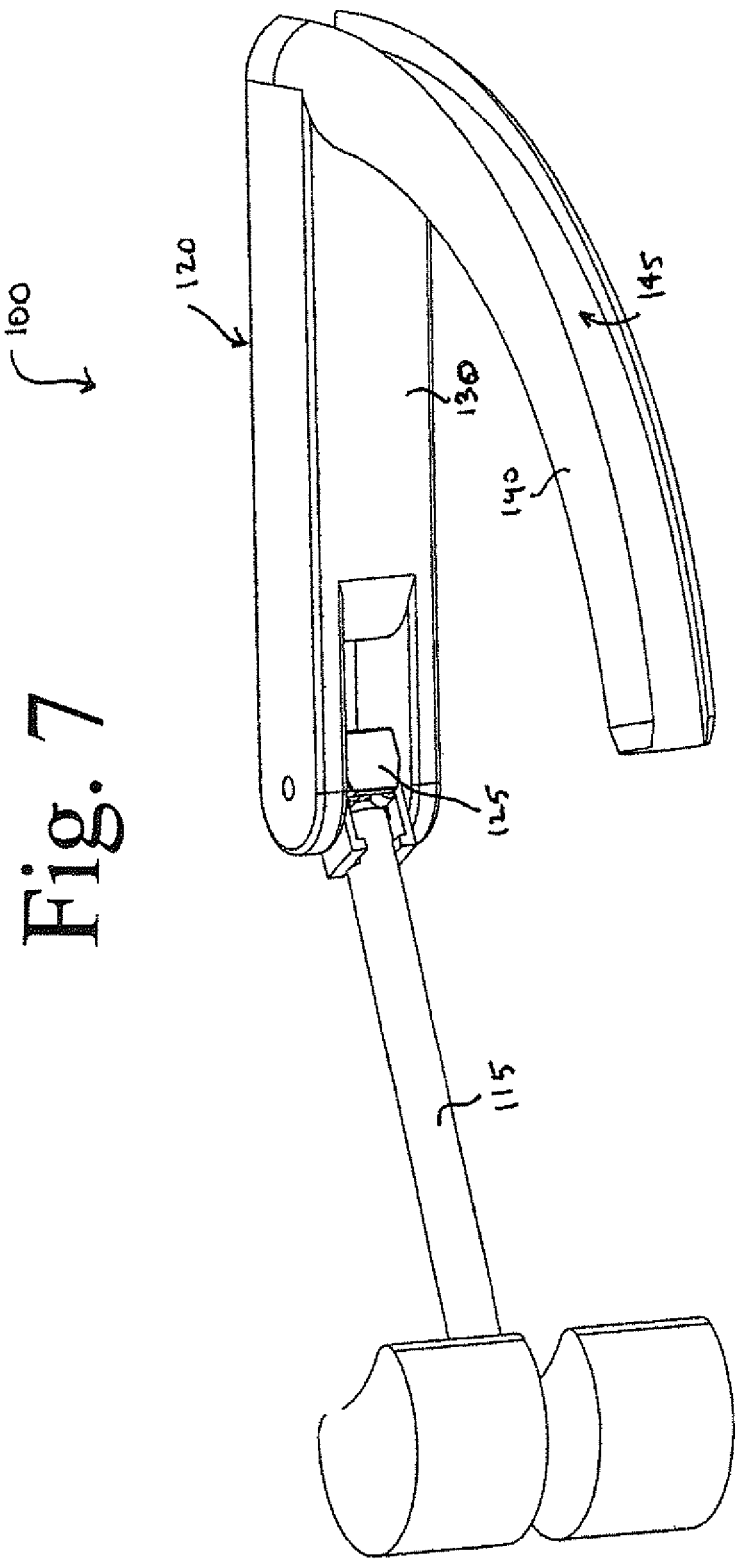
FIG. 7 shows a perspective view of the device with the insertion device pivotably attached to the mount via the attachment member.

FIG. 7 shows a perspective view of the device 100 with the insertion device 120 pivotably attached to the mount 115 via the attachment member 125. As mentioned, the insertion device 120 includes a curved portion 140 having a guide shaft 145 that extends through the length of the curved portion 140. The guide shaft 145 has an open end such that the guide shaft 145 is visible from the side of the curved portion 140.

Figure 8:
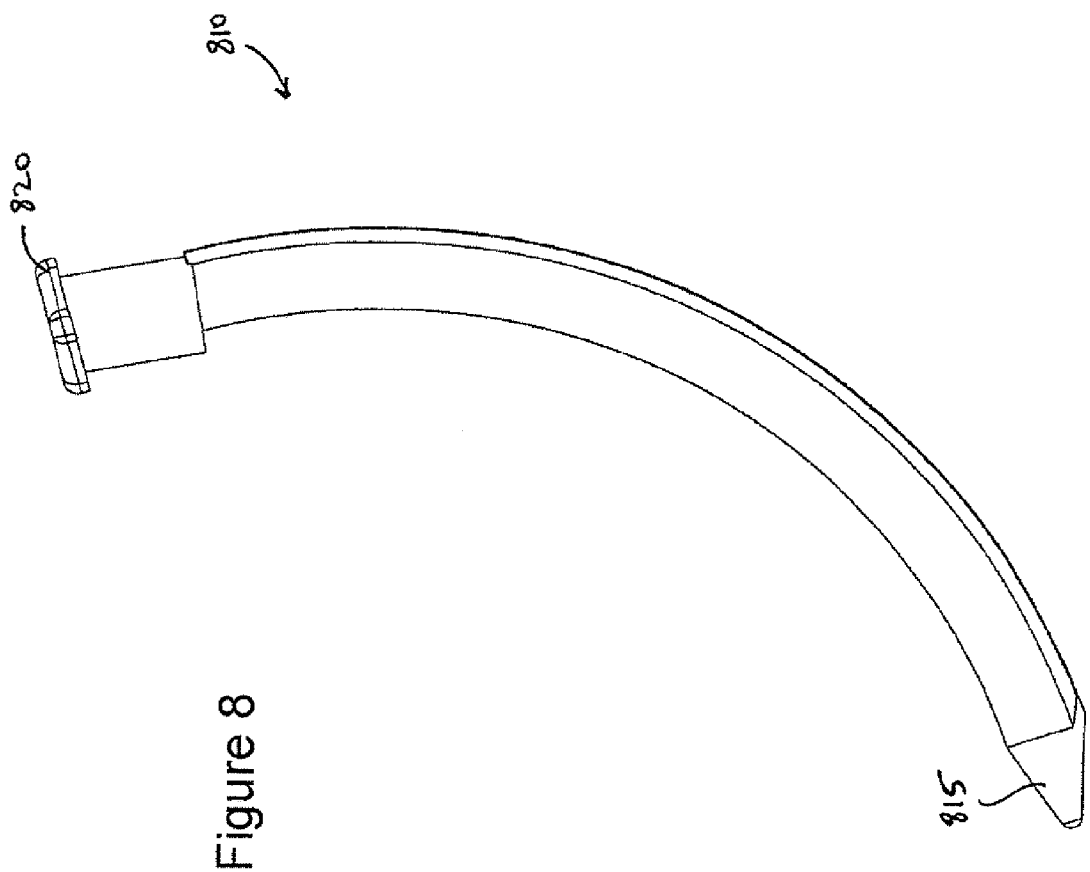
FIG. 8 shows a side view of an elongate plunger of the device.
Figure 9:
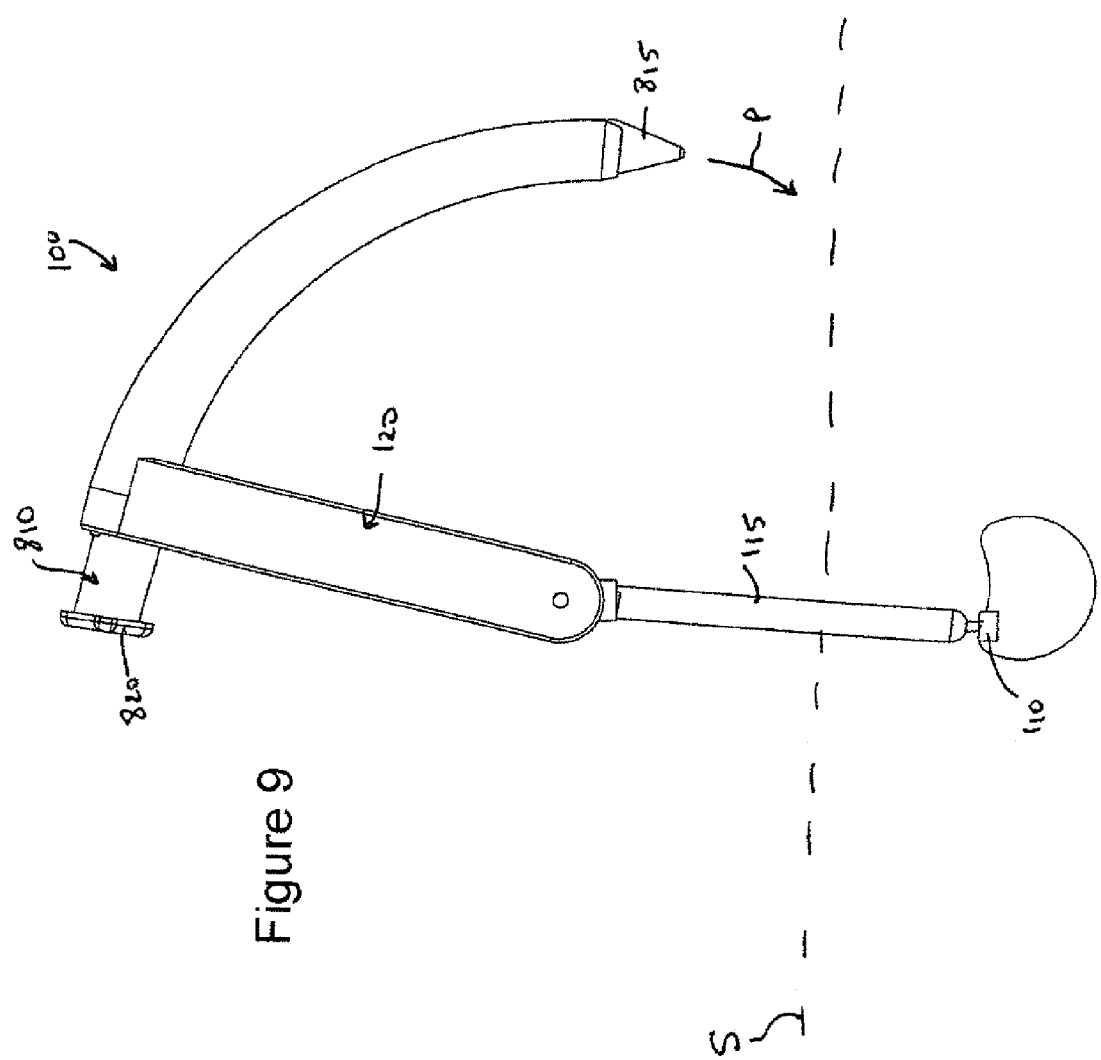
FIG. 9 shows a side view of the device with the plunger positioned inside a slot of the insertion device.

FIG. 8 shows a side view of an elongate plunger 810 that slidably fits within the guide shaft 145 of the curved portion 140 of the insertion device 120. The plunger 810 has a tapered tip 815 on a distal end and a handle 820 on a proximal end. The plunger 810 is inserted into the guide shaft 145 by inserting the tapered tip 815 into an entryway (shown in FIG. 1) of the guide shaft 145 and sliding the plunger 810 into the guide shaft 145. When the plunger 810 is fully positioned in the guide shaft 145, the handle 820 protrudes out of one end of the guide shaft 145 and the tapered tip 81-5 protrudes out of the opposite end of the guide shaft 145. FIG. 9 shows a side view of the device 100 with the plunger 810 positioned inside the slot 140 of the insertion device 120.

An exemplary method of using the device 100 is now described in the context of using the device 100 to implant of an implant device between a pair of vertebrae. First, the spine is approached through a posterior incision permitting access to the inter-vertebral disc space through a window lateral to the nerves. A discectomy is performed and the disc material is removed piecemeal.

Figure 10A:
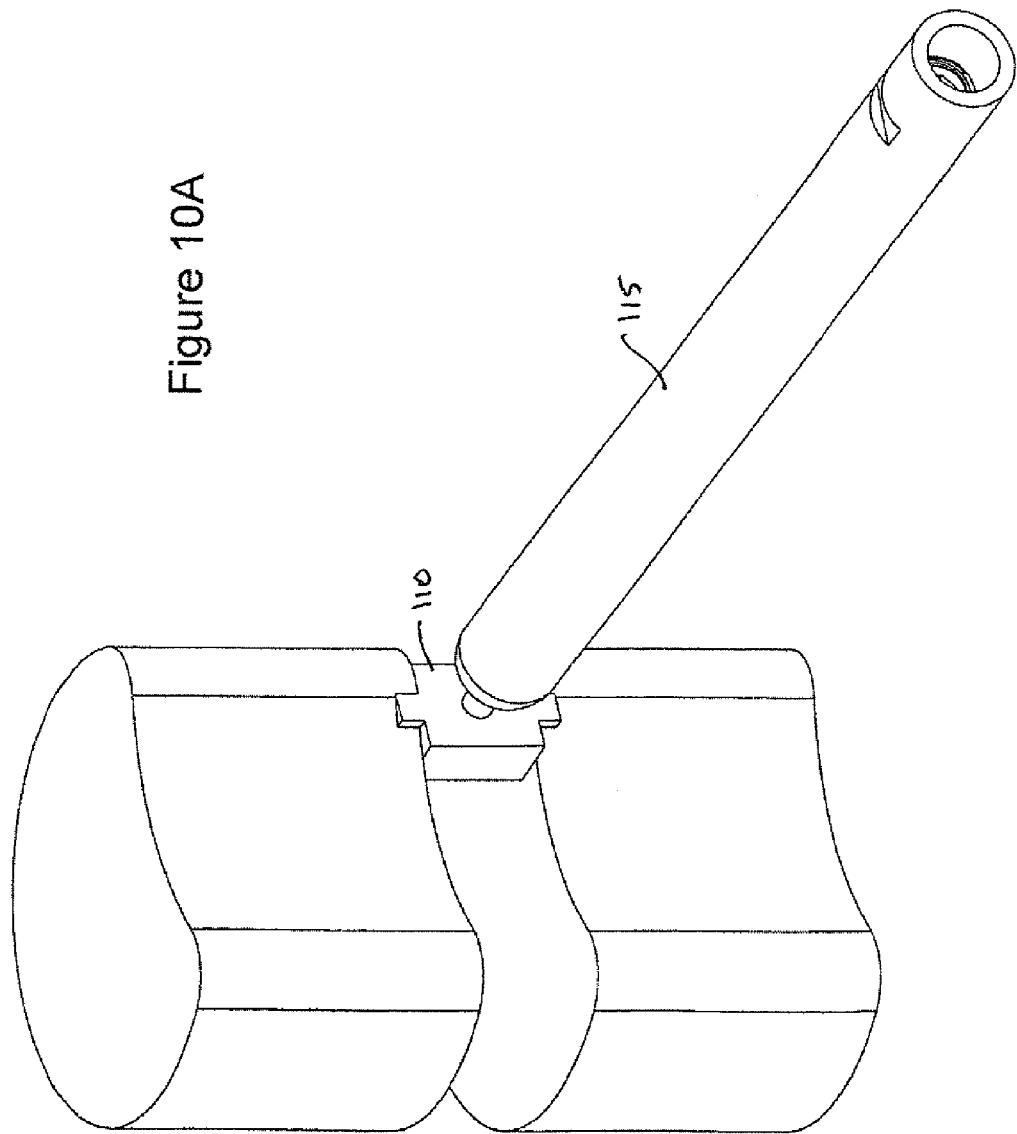
FIG. 10A shows a perspective view of the mount attached to a disc space.

The coupler 110 of the device 100 is then attached to an attachment point. It should be appreciated that the attachment point need not be the disc space itself. The coupler 110 can be attached directly to one of the vertebrae or to some other reference location. In an exemplary embodiment, the coupler 110 is tightly fitted into the disc space between the vertebrae such that the coupler is anchored in the disc space. During this step, the insertion device 120 can be disattached from the mount 115 such that the proximal end of the mount 115 is free and the distal end of the mount 115 is attached to the coupler 110. At this stage, the mount 115 extends outwardly from the coupler 110, as shown in FIG. 10A.

After the distal end of the mount 115 is tightly fitted into the disc space, a target location is identified and localized, wherein the target location is the location where the implant device is to be implanted. The mount 115 is positioned such that the insertion device 120, when attached to the mount 115, can be pivoted to an orientation that provides a guide toward the target location for delivery of the implant device. In this regard, the mount 115 can be aimed toward the target location in a variety of manners. For example, one or more x-ray image can be taken of the target location and the target location localized using the x-ray images by iteratively moving the mount so that the insertion device provides a guide toward the target location. A pointer, such as an elongate needle, can be used in combination with the one or more x-ray images to aid in pointing the mount and insertion device toward the target location. The mount can also be attached directly at the target location (such as in the disc space) to facilitate localization of the target location. The insertion device 120, when connected to the mount 115 and coupler 110, is movable in a fixed geometric relationship to the mount and coupler 110 so as to place the implant at the target location.

In one embodiment, the free, proximal end of the mount 115 is moved into the spinal midline by pivoting the mount about its attachment location with the coupler 110. The spinous process is easily located on the posterior aspect of the spine and it marks the midline. In another embodiment, another portion of the device clamps onto the spinous processes and act as a marker of midline the attachment point for the swing arm.

Once the mount 115 is positioned in the desired orientation (such as with the free end of the mount along the spinal midline), the inner member 315 (FIG. 3) of the mount 115 is rotated relative to the outer member 310. This locks the position and orientation of the mount. At this stage, the mount is positioned along the spinal midline.

In addition, the mount 115 is now appropriately positioned and locked in this position. The insertion device 120 can now be attached to the free, proximal end of the mount 115. At this stage, the assembled device 100 is coupled to the disc space such that the mount 115 extends outwardly from the disc space and the insertion device 120 is pivotably mounted to the proximal end of the mount 115.

The plunger 810 is then slid into the curved guide shaft 145 of the insertion device 120, as shown in FIG. 9. The handle 820 of the plunger 810 is then used to push the insertion device 120 such that the insertion device 120 rotates toward the skin S about the pivot axis R, as represented by the arrow P in FIG. 9. As the rotational movement occurs, the tapered tip 815 of the plunger 810 moves toward the skin S and eventually abuts the skin S. A small skin incision is made and the insertion device 120 is then rotated further until the tapered tip 815 contacts the lateral side of the disc space.

Figure 10B:
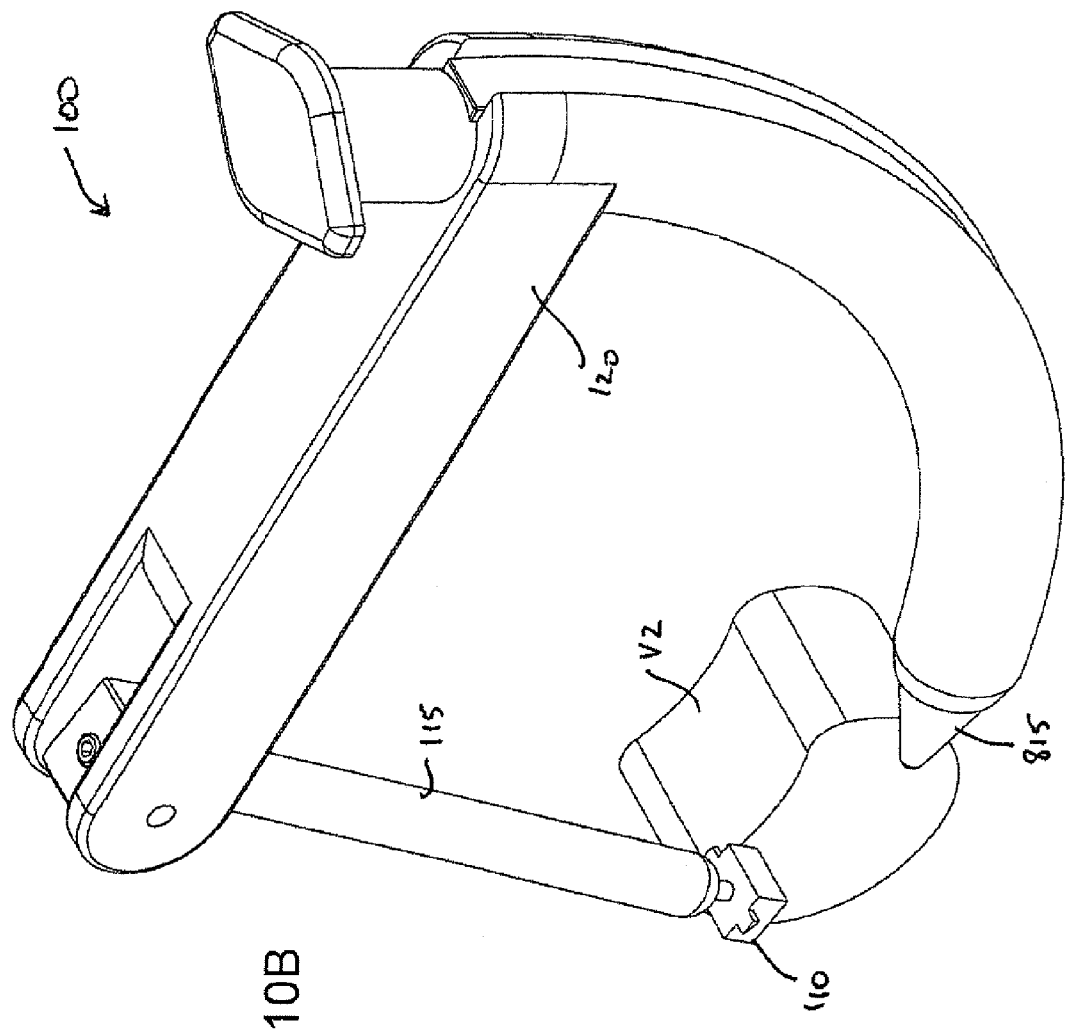
FIG. 10B shows a perspective view of the device with the insertion device fully rotated toward the disc space such that a tapered tip is positioned adjacent the lateral side of the disc space between the vertebrae.

FIG. 10B shows a perspective view of the device 100 with the insertion device 120 fully rotated toward the disc space such that the tapered tip 815 is positioned adjacent the lateral side of the disc space between the vertebrae. For clarity of illustration, the skin S is not shown in FIG. 10 and the first vertebra Vi is also not shown.

The plunger 810 is now removed from the guide shaft 145 such that the slot is empty. FIG. 11 shows an enlarged, close-up view with the distal tip of the insertion device 120 positioned adjacent the lateral side of the disc space between the vertebrae. Although shown adjacent to the posterior end of the disc space, it should be appreciated that the insertion device 120 can be positioned adjacent to any part of the disc space.

At this stage, the guide shaft 145 provides a pathway to the target location (e.g., the disc space). An implant device can now be delivered into the disc space by sliding the implant device through the guide shaft 145 in the curved portion 140 of the insertion device 120. In this way, an orthopedic device can be precisely delivered into the inter-vertebral disc space using the posterior surgical approach with minimal tissue dissection or nerve retraction. This method provides a minimally invasive way of implanting orthopedic devices into the disc space.

Figure 12:
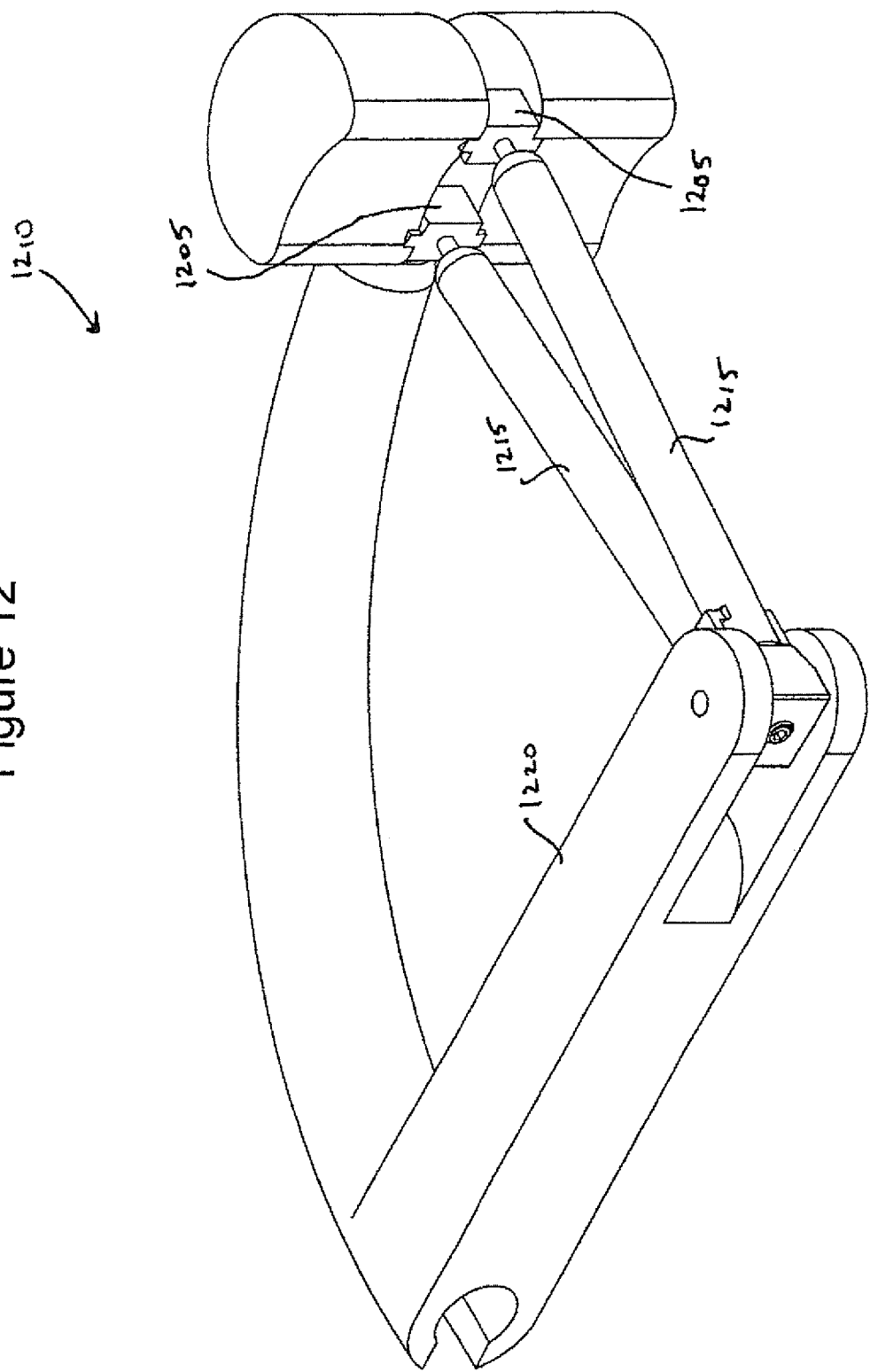
FIG. 12 shows a perspective, assembled view of a second embodiment of the device.
Figure 13:
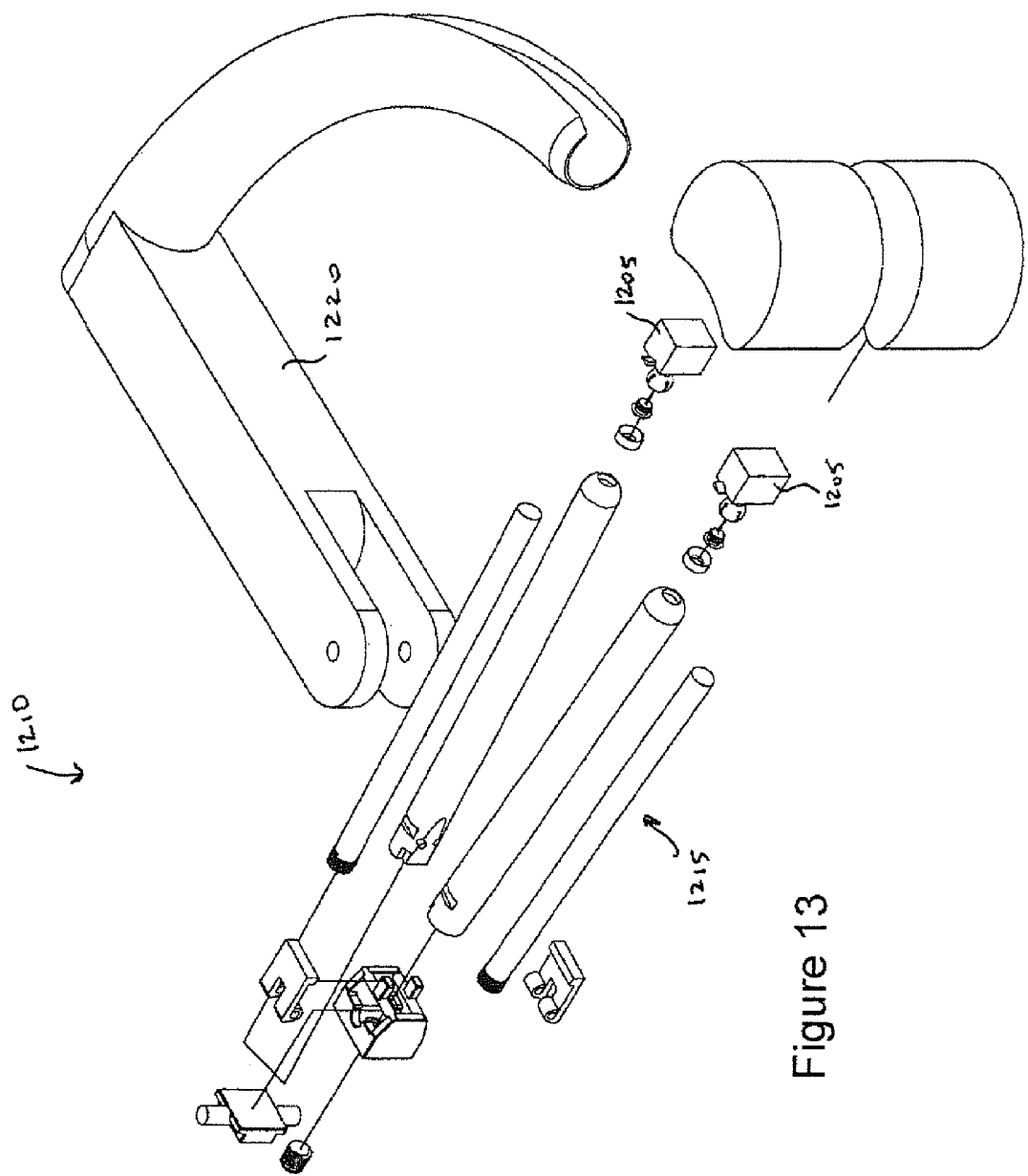
FIG. 13 shows an exploded view of the second embodiment of the device.

FIG. 12 shows a perspective, assembled view of a second embodiment of the device, referred to as device 1210. FIG. 13 shows an exploded view of the second embodiment of the device 1210. In this embodiment, the device 1210 includes a pair of mounts 1215 that anchor the device 1210 within the disc space between two vertebrae. As in the previous embodiment, the mounts 1215 are elongate rods that are each attached at one end to a coupler 1205. The proximal ends of the mounts 1215 are joined to an insertion device 1220 in a pivoting manner using an attachment member 1225. Since both mounts 1215 are of equal length, the distal ends are in the spinal midline.

It should be appreciated that the configuration of the devices and the methods described herein can vary. For example, in another embodiment, a member is attached onto the spinous processes and define the midline. An instrument is placed into the disc space, coupled to the spinous process member and used to determine the plane of the disc space. The insertion device is then attached onto one or both of these segments and rotated onto the lateral aspect of the disc space as illustrated above. In other embodiments, the pedicles or other bony landmarks are used as attachment points. The insertion device is then fixed to the attached member and rotated onto the lateral aspect of the disc space as previously described.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. A method for delivery of an orthopedic implant onto a target intervertebral disc space of a subject, the method comprising:

approaching the target intervertebral disc space through a posterior skin incision and a surgical corridor;

performing at least a partial discectomy through a posterior window immediately lateral to nerve elements adjacent to the target intervertebral disc space;

positioning a segment of an implant insertion member in proximity to a site of the discectomy, the implant insertion member comprising an elongated body extending along a curvilinear trajectory, the elongated body comprising an internal bore configured to permit advancement of the orthopedic implant therethrough;

attaching a first end of a fixation member to a proximal segment of the implant insertion member, the fixation member comprising a locking feature configured to reversibly immobilize the first end of the fixation member and at least a portion of the implant insertion member;

attaching a second end of the fixation member rigidly onto a coupling apparatus having a defined spatial relationship to the target intervertebral disc space, attachment thereof limiting movement of the implant insertion member relative to the target intervertebral disc space in at least one plane;

rotating the implant insertion member relative to the fixation member from a location outside the subject to a lateral side aspect of the target intervertebral disc space; and advancing the orthopedic implant through the internal bore of the implant insertion member and onto the target intervertebral disc space.

2. The method of claim 1, further comprising identifying the target intervertebral disc space using an imaging technique.

3. The method of claim 1, wherein the act of attaching a first end of a fixation member to a proximal segment of the implant insertion member comprises attaching thereto at a distal aspect of a straight segment of the implant insertion member from which the elongated body is configured to extend from outwardly in a first direction.

4. The method of claim 3, wherein the curvilinear trajectory of the elongated body forms a circumference of a circle having a radius substantially equal to a length of the straight segment.

5. The method of claim 1, wherein the act of advancing the orthopedic implant onto the target intervertebral disc space comprises advancement thereof along the curvilinear trajectory.

6. The method of claim 1, attaching a first end of a fixation member to a proximal segment of the implant insertion member comprises forming a movable articulation therebetween.

7. The method of claim 6, wherein the movable articulation comprises a ball and socket joint.

8. The method of claim 1, wherein the fixation member further comprises a deployable locking mechanism configured to reversibly transition from a first configuration in which first and second segments of the fixation member are movable relative to one another, to a second configuration in which the first and second segments are immobilized.

9. The method of claim 1, further comprising positioning, prior to rotation of the implant insertion member relative to the fixation member, the center of rotation substantially over a spinal midline, the spinal midline being defined as a sagittal plane dividing a target spinal segment into a right portion and a left portion.

10. The method of claim 1, further comprising containing a plunger at least partially within the internal bore while the implant insertion member is positioned onto a target location.

11. The method of claim 10, further comprising removing the plunger from within the internal bore in order to allow passage of the orthopedic implant onto the target location.

12. A method for delivery of an orthopedic implant onto a target intervertebral disc space of a subject, comprising:
performing at least a partial discectomy through a window immediately lateral to nerve elements proximate to the target disc space;
positioning a segment of an implant insertion member in proximity to the target disc space;
attaching a first end of a fixation member to a proximal segment of the implant insertion member, the attachment permitting reversible immobilization of the first end of the fixation member and the proximal segment of the implant insertion member;
rigidly attaching a second end of the fixation member onto a first surface having a defined, spatial relationship to the target disc space, the attachment limiting movement of the implant insertion member relative to the target disc space in at least one plane; and
advancing the orthopedic implant through an internal bore of the implant insertion member and onto a lateral side aspect of the target disc space;

wherein the implant insertion member comprises an elongated body extending along a first direction from a proximal segment to a distal segment; and
wherein the elongated body comprises the internal bore, and the internal bore is configured to extend at least partially along the first direction in a curvilinear trajectory.

13. The method of claim 12, further comprising identifying the target disc space using an imaging technique.

14. The method of claim 12, wherein the act of attaching the first end of a fixation member to the proximal segment of the implant insertion member comprises attachment thereto at a distal aspect of a straight segment of the implant insertion member from which the elongated body is configured to extend outwardly from.

15. The method of claim 14, wherein the elongated body is further configured to at least substantially fount a circumference of a circle having a radius substantially equal to the straight segment.

16. The method of claim 12, wherein the act of advancing the orthopedic implant onto the target disc space comprises causing the orthopedic implant to follow the curvilinear trajectory of the internal bore.

17. The method of claim 12, further comprising forming a movable articulation between first and second segments of the fixation member.

18. The method of claim 17, further comprising deploying a locking mechanism of the fixation member, the locking mechanism configured to reversibly transition from a first configuration in which the first and second segments are movable, to a second configuration in which the first and second segments are immobilized relative to one another.

19. The method of claim 12, further comprising placing a plunger at least partially within the internal bore while the implant insertion member is positioned onto the target disc space.

20. The method of claim 19, further comprising removing the plunger from within the internal bore in order to allow passage of the orthopedic implant onto the target disc space.

21. The method of claim 12, wherein the act of attaching a first end of a fixation member to a proximal segment of the implant insertion member further comprises substantially positioning the attachment over a spinal midline, the spinal midline being defined as a sagittal plane dividing a target spinal segment into a right portion and a left portion.

22. The method of claim 12, further comprising anchoring a coupler within the target disc space, the coupler comprising the first surface having the defined spatial relationship to the target disc space, and the second end of the fixation member attaching onto the first surface.

23. The method of claim 22, wherein the act of anchoring the coupler comprises removably securing the coupler within the target disc space.

24. A method for delivery of an orthopedic implant onto a target intervertebral disc space of a subject, the target intervertebral disc space being accessible through a skin incision and a surgical corridor, the method comprising;
performing at least a partial discectomy through a posterior window lateral to nerve elements adjacent to the target intervertebral disc space;
positioning a segment of an implant insertion member in proximity to a site of the discectomy, the implant insertion member comprising an elongated body extending along an at least partly curvilinear trajectory, the elongated body comprising an internal bore configured to permit advancement of the orthopedic implant therethrough;

attaching a first end of a fixation member to a segment of the implant insertion member, the fixation member comprising a locking feature configured to reversibly immobilize the first end of the fixation member and at least a portion of the implant insertion member;

attaching a second end of the fixation member rigidly onto a coupling apparatus having a spatial relationship to the target intervertebral disc space, attachment thereof limiting movement of the implant insertion member relative to the target intervertebral disc space in at least one plane;

rotating the implant insertion member relative to the fixation member to a lateral side aspect of the target intervertebral disc space; and advancing the orthopedic implant through the internal bore of the implant insertion member and into the target intervertebral disc space.

* * * * *